United States Patent [19]

Hjerten

[11] Patent Number: 5,221,447
[45] Date of Patent: Jun. 22, 1993

[54] HYDROPHILIC POLYMER COATING OF HIGH PH STABILITY FOR SILICA SURFACES FOR SUPPRESSION OF ELECTROENDOMOSIS AND SOLUTE ADSORPTION

[75] Inventor: Stellan Hjerten, Uppsala, Sweden

[73] Assignee: Bio-Rad Laboratories, Inc., Hercules, Calif.

[21] Appl. No.: 804,313

[22] Filed: Dec. 6, 1991

[51] Int. Cl.$^5$ .................... G01N 27/26; G01N 27/447
[52] U.S. Cl. .............................. 204/180.1; 204/299 R
[58] Field of Search ......................... 204/180.1, 299 R

[56] References Cited

U.S. PATENT DOCUMENTS

| | | | |
|---|---|---|---|
| 4,680,201 | 7/1987 | Hjerten | 204/182.9 X |
| 4,690,749 | 9/1987 | Van Alstine et al. | 204/300 EC X |
| 5,082,559 | 1/1992 | Eguchi et al. | 210/198.3 X |

Primary Examiner—John Niebling
Assistant Examiner—John S. Starsiak, Jr.

[57] ABSTRACT

Silica-containing surfaces, such as the inner wall of a quartz or fused silica capillary used in capillary electrophoresis, are activated by a suitable linking agent which combines with the silanol groups on the surface to form Si—O—Si linkages leaving vinyl or acryl groups on the linking agent exposed for further reaction. A suitably derivatized hydrophilic polymer is then coupled to the linking agent to from a polymeric coating over the surface. The coating remains hydrophilic throughout the coupling process, and the coupling is unusually stable at pH's of 12 and above.

13 Claims, 1 Drawing Sheet

HYDROPHILIC POLYMER COATING OF HIGH PH STABILITY FOR SILICA SURFACES FOR SUPPRESSION OF ELECTROENDOMOSIS AND SOLUTE ADSORPTION

This invention lies in the field of electrophoresis, and relates in particular to electrophoresis in capillaries which have been coated for purposes of suppressing electroendosmosis and solute adsorption.

BACKGROUND OF THE INVENTION

The ideal electrophoresis procedure, particularly in capillaries, is one in which the resolution of the solute zones is not lessened by either electroendosmosis or solute adsorption at the wall of the capillary or other electrophoresis chamber. If the effect of electroendosmosis were to produce a perfect plug flow, the only result would be a displacement of the solute zones with no effect on resolution. Electroendosmosis has, however, been found to cause zone deformation and a loss of resolution. With capillaries whose inner wall surfaces have been coated with a polymer to suppress electroendosmosis, it has also been noticed that the solute zones broaden with repeated use of the capillary. One explanation is the gradual deterioration of the coating upon exposure to the high pH conditions involved in electrophoretic procedures. An alternative explanation is solute adsorption by the coating upon repeated use. The adsorbed solutes place charges on the wall surface, the charges themselves giving rise to electroendosmosis.

Hjertén, U.S. Pat. No. 4,680,201, Jul. 14, 1987, discloses the application of a thin coating of an uncharged polymer to the capillary wall. The polymer commonly used for this purpose is linear polyacrylamide, and the effect of the polymer coating is to eliminate electroendosmosis and suppress adsorption. Experiments have shown that the polyacrylamide coating is stable for at least four weeks (the test period) at pH 11, but for only a few hours at pH 12. The reason is that acrylamide bonds tend to hydrolyze at high pH. The ability to withstand high pH conditions is important since wash solutions at pH 12-13 are needed for releasing adsorbed solutes.

This and other problems encountered in the prior art are addressed by the present invention.

SUMMARY OF THE INVENTION

It has now been discovered that hydrophilic polymers can be coupled to the surface of a silica-containing capillary in such a manner that the hydrophilicity of the polymer is retained despite the coupling. It has also been discovered that the coupling remains stable at pH values of 12 or higher. The coupling is achieved through a Si—O—Si bond. While hydrophilic polymers themselves are known to be pH-stable, it is surprising and unexpected that the polymers do not become detached from the wall under these high pH conditions, since the Si—O—Si bond is generally believed to be susceptible to hydrolysis when exposed to alkaline conditions. This susceptibility to hydrolysis is why silica columns, widely used in chromatography, are not recommended for use at pH conditions higher than pH 8.

In addition to the bond stability at high pH, the present invention offers the further advantage of the hydrophilic nature of the coating which avoids any hydrophobic interactions with nonpolar residues of the solutes being separated.

DETAILED DESCRIPTION OF THE INVENTION AND PREFERRED EMBODIMENTS

Figure 1:
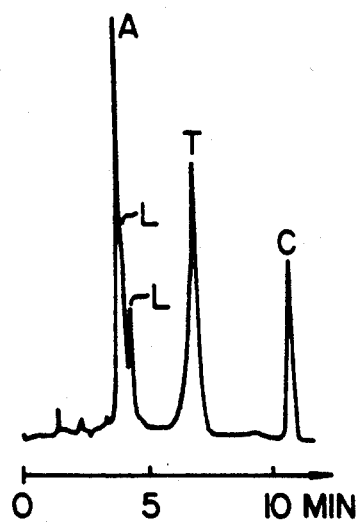
FIG. 1 is a detector trace of an electropherogram generated by an electrophoretic experiment using a capillary tube coated in accordance with the present invention.

Silica-containing surfaces to which the present invention applies may be any form of silica suitable for use as a chamber for electrophoresis. Prominent examples are quartz and fused silica. The electrophoresis medium itself may be in the form of a slab, a tube or a capillary. The invention is of particular interest in connection with capillary electrophoresis.

A wide variety of hydrophilic polymers may be used. Examples are methyl cellulose, poly(vinyl alcohol), dextran, starch and agarose.

The coupling of the hydrophilic polymer to the silica wall surface is achieved through a linking agent which contains two functional groups, one of which forms a Si—O—Si bond at the wall surface and the other adjoins the polymer in a manner which preserves the hydrophilic nature of the polymer. The first functional group is preferably an acetoxysilane, chlorosilane, or alkoxysilane group. The second functional group is preferably a vinyl or acryl group. Methacryl-terminated trimethoxysilanes are a preferred class, and methacryloxypropyltrimethoxysilane is a preferred example.

To facilitate coupling, the hydrophilic polymer either contains, or is derivatized to contain, a terminal moiety which reacts with the second functional group of the linking agent. Examples are allyl and acryl groups. Derivatization of the polymer to attach such a group can be performed in accordance with methods known among those skilled in the art. The hydrophilic nature of the polymer may for example be maintained by using a derivatizing agent which contains a terminal epoxy (i.e., ethylene oxide) group to react with a native hydroxyl group on the polymer. An example of such a derivatizing agent is allyl glycidyl ether, with the terminal epoxy group of the glycidyl moiety reacting with the hydroxyl group of the polymer, leaving the allyl group available for coupling to the second functional group of the linking agent.

With linking agents in which the first functional group is a methoxy group (for example, methacryl-terminated trimethoxysilanes), the methoxy groups react with the silanol groups on the wall surface to form Si—O—Si bonds which, as indicated above, are unusually stable at high pH when linked to a polymer coating in accordance with this invention.

The reactions involved in the practice of this invention are performed in accordance with known techniques which will be readily apparent to those skilled in the art. In the polymer derivatization reaction, for example, a conventional reducing agent is used. For methyl cellulose and most other hydrophilic polymers, sodium borohydride is one example of a reducing agent. For polyvinyl alcohol, a more suitable reducing agent would be a stream of nitrogen. The coupling of the derivatized polymer to the activated silica surface is performed in the presence of a polymerization catalyst such as N,N,N',N'-tetramethylethylenediamine (TEMED) and ammonium persulfate, and the reaction generally involves the further polymerization of the polymer in addition to the coupling of the polymer to the activated surface.

The following example is offered strictly for purposes of illustration, and is intended neither to limit nor to define the invention in any manner.

EXAMPLE

The capillary tubing used in the following experiment was fused silica with an inner diameter of 0.05 mm and a length of 15 cm, obtained from Polymicro Technologies Inc., Phoenix, Ariz., U.S.A. The methyl cellulose was obtained from Dow Chemical Company, Midland, Mich. U.S.A., and was characterized by the supplier as having a viscosity of 7,000 cps. The sodium borohydride was obtained from Merck, Schuchardt, Germany. The ammonium persulfate, N,N,N',N'-tetramethylethylenediamine (TEMED), agarose (zero-$m_r$) and sodium dodecyl sulfate (SDS) were obtained from Bio-Rad Laboratories, Inc. Hercules, Calif., U.S.A. The γ-methacryloxypropyltrimethoxysilane was obtained from LKB, Bromma, Sweden, and the allyl glycidyl ether was obtained from Aldrich Chemie, Steinheim, Germany.

A. Pretreatment of the Inner Surface of the Capillary

The tube was first washed with water, then filled with 0.1M sodium hydroxide and let stand for five minutes, although longer times are sometimes preferable. The sodium hydroxide was then removed, and the tube was flushed with water, then with 0.1M hydrochloric acid, and finally with water again.

B. Activation of the Inner Wall of the Capillary with Methacryl Groups

The capillary was filled with a solution prepared by mixing 4 μL of γ-methacryloxypropyltrimethoxysilane with 1 mL of acetic acid (pH 3.0). The solution was retained in the capillary for 20 hours, then displaced with water.

C. Derivatization of the Hydrophilic Polymer (Methyl Cellulose)

A freshly prepared 2.5M solution of sodium hydroxide containing 0.2 g sodium borohydride was added to a 2% (weight/volume) solution of methyl cellulose, with stirring. Achieving a homogeneous solution required stirring for about ten minutes due to the high viscosity of the polymer solution. Once the solution was homogeneous, allyl glycidyl ether (2 mL) was added. Stirring was then continued for an additional twenty hours as the hydroxyl groups in the methyl cellulose reacted with the epoxy groups in the allyl glycidyl ether. The solution was the dialyzed repeatedly against distilled water until the pH was 5–6. (Note that due to the uptake of carbon dioxide from the air, the pH of the distilled water was not neutral.)

D. Coupling of Allyl Methyl Cellulose to the Methacryl-Activated Inner Wall of the Capillary A solution was prepared by mixing 500 μL of a 0.7% (weight/volume) solution of the allyl-derivatized methyl cellulose prepared as described in the preceding section with 7.5 μL of a fresh 10% (weight/volume) aqueous solution of ammonium persulfate. The solution was deaerated, and 7.5 μL of a 5% (volume/volume) solution of TEMED was added. The solution was then drawn into the capillary tube. The reaction started after 1–2 hours and was permitted to run for a total of ten hours. The polymerized solution was then pressed out of the capillary by an HPLC (high-performance liquid chromatography) pump, and replaced with a solution freshly prepared by mixing one volume of 10% (weight/volume) SDS with one volume of a 0.01M sodium hydroxide solution (pH 12). This solution had a pH of 11.7.

E. Test of the Stability of the Coating Under Harsh Conditions

As indicated above, the length of the methyl cellulose coated tube was 15 cm and the inner diameter was 0.05 mm. The electrophoretic migration distance was 11 cm. The tube was filled with 0.05M glycine-NaOH, pH 9.8. One end of the tube was then closed with a plug of 1.5% (weight/volume) agarose gel, prepared in the electrophoresis buffer, to prevent hydrodynamic flow in the tube during electrophoresis and accordingly any displacement of the solute zones which would be attributable to such flow.

A test sample was prepared, consisting of human serum albumin, bovine β-lactoglobubin, human transferrin and bovine carbonic anhydrase, dissolved in the electrophoresis buffer, diluted ten-fold. The concentration of transferrin was 0.46 mg/mL, and the concentration of each remaining protein was 0.23 mg/mL.

The test sample was introduced into the end of the capillary which had not been plugged, and which served as the cathodic end, by electrophoresis at 3,000 V for 8 sec. Electrophoretic separation was then performed in a series of runs at the same voltage on portions of the same sample.

Figure 2:
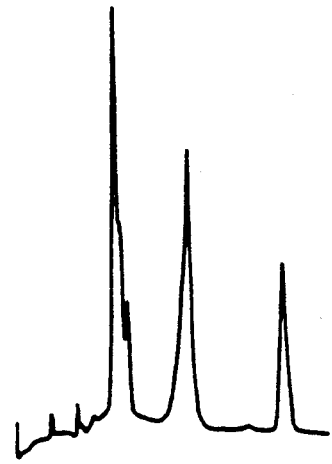
FIG. 2 is a detector trace of the electropherogram of a repeat experiment identical to that of FIG. 1 after several intervening repeat experiments with the same coated capillary.
Figure 3:
FIG. 3 is a detector trace of the electropherogram of a further repeat experiment identical to those of FIGS. 1 and 2 after several more intervening repeat experiments with the same coated capillary.

Prior to the first run, the capillary was exposed to a 5% SDS solution at pH of about 12 for two days. The resulting electropherogram is shown in FIG. 1, in which the peaks are labeled as follows:
A: albumin
L: β-lactoglobulin
T: transferrin
C: carbonic anhydrase Over a period of two weeks after the first run, the experiment was repeated 1–4 times every day. Between each run the capillary was flushed with the 5% SDS solution at pH of about 12 and let stand with the solution inside the capillary. Prior to each run, the capillary was washed with water, 0.1M sodium phosphate (pH 2.5), water again, and finally electrophoresis buffer. FIGS. 2 and 3 are electropherograms taken at ten days (the twenty-second run) and sixteen days (the fifieth run), respectively, counting from the initial exposure of the capillary to the 5% SDS solution. It is clear from a comparison of the electropherograms that the coating exhibited a high degree of stability despite the harsh treatment suffered by the exposure to SDS and the high pH.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

What is claimed is:

1. A method of treating a silica-containing wall to inhibit electroendosmosis and solute adsorption at said wall during electrophoresis through a medium retained by said wall, said method comprising:
   (a) bonding a linking agent which is a member selected from the group consisting of vinyl-terminated acetoxysilanes, vinyl-terminated chlorosilanes, vinyl-terminated alkoxysilanes, acryl-terminated acetoxysilanes, acryl-terminated chlorosilanes and acryl-terminated alkoxysilanes, to silicon atoms on said wall by forming a Si—O—Si bond, thereby forming a coating on said wall with exposed vinyl or acryl groups; and
   (b) bonding to said wall a hydrophilic polymer selected from the group consisting of methyl cellulose, poly(vinyl alcohol), dextran, starch and agarose, each of which is derivatized to contain terminal allyl or acryl moieties, by reacting said terminal moieties with said exposed vinyl or acryl groups, thereby forming a coating of said hydrophilic polymer over said wall.

2. A method in accordance with claim 1 in which said terminal moieties of said hydrophilic polymer are allyl groups.

3. A method in accordance with claim 1 in which said hydrophilic polymer is a member selected from the group consisting of allyl-terminated methyl cellulose, allyl-terminated poly(vinyl alcohol), allyl-terminated dextran, allyl-terminated starch and allyl-terminated agarose.

4. A method in accordance with claim 1 in which said hydrophilic polymer is a member selected from the group consisting of methyl cellulose, poly(vinyl alcohol), dextran, starch and agarose, each of which has been derivatized by reaction with allyl glycidyl ether.

5. A method in accordance with claim 1 in which said linking agent is a methacryl-terminated trimethoxysilane.

6. A method in accordance with claim 1 in which said linking agent is methacryloxypropyltrimethoxysilane.

7. A method of treating the interior surface of a silica-containing wall of a chamber to inhibit electroendosmosis and solute adsorption at said interior surface during electrophoresis through a medium retained in said chamber, said method comprising:
   (a) bonding a linking agent which is a member selected from the group consisting of vinyl-terminated acetoxysilanes, vinyl-terminated chlorosilanes, vinyl-terminated alkoxysilanes, acryl-terminated acetoxysilanes, acryl-terminated chlorosilanes and acryl-terminated alkoxysilanes, to silicon atoms on said interior surface by forming a Si—O—Si bond, thereby forming a coating on said interior surface with exposed vinyl or acryl groups; and
   (b) bonding to said interior surface a hydrophilic polymer containing terminal moieties selected from the group consisting of allyl and acryl groups, said hydrophilic polymer having been formed outside said chamber, by placing said hydrophilic polymer inside said chamber and reacting said terminal moieties with said exposed vinyl or acryl groups, thereby forming a coating of said hydrophilic polymer over said interior surface.

8. A method in accordance with claim 7 in which said hydrophilic polymer is a member selected from the group consisting of methyl cellulose, poly(vinyl alcohol), dextran, starch and agarose, each of which is derivatized to contain terminal allyl or acryl moieties.

9. A method in accordance with claim 7 in which said terminal moieties of said hydrophilic polymer are allyl groups.

10. A method in accordance with claim 7 in which said hydrophilic polymer is a member selected from the group consisting of allyl-terminated methyl cellulose, allyl-terminated poly(vinyl alcohol), allyl-terminated dextran, allyl-terminated starch and allyl-terminated agarose.

11. A method in accordance with claim 7 in which said hydrophilic polymer is a member selected from the group consisting of methyl cellulose, poly(vinyl alcohol), dextran, starch and agarose, each of which has been derivatized by reaction with allyl glycidyl ether.

12. A method in accordance with claim 7 in which said linking agent is a methacryl-terminated trimethoxysilane.

13. A method in accordance with claim 7 in which said linking agent is methacryloxypropyltrimethoxysilane.

* * * * *